US012585104B2

(12) United States Patent
Satake

(10) Patent No.: US 12,585,104 B2
(45) Date of Patent: Mar. 24, 2026

(54) IMAGE PICKUP MODULE, ENDOSCOPE, AND METHOD FOR MANUFACTURING IMAGE PICKUP MODULE

(71) Applicant: OLYMPUS MEDICAL SYSTEMS CORP., Tokyo (JP)

(72) Inventor: Nau Satake, Yokohama (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 121 days.

(21) Appl. No.: 18/786,947

(22) Filed: Jul. 29, 2024

(65) Prior Publication Data

US 2025/0044572 A1 Feb. 6, 2025

Related U.S. Application Data

(60) Provisional application No. 63/530,538, filed on Aug. 3, 2023.

(51) Int. Cl.

| | |
|---|---|
| ***G02B 23/24*** | (2006.01) |
| ***A61B 1/00*** | (2006.01) |
| ***A61B 1/05*** | (2006.01) |
| ***H04N 23/50*** | (2023.01) |

(52) U.S. Cl.

CPC ........ *G02B 23/2484* (2013.01); *A61B 1/0011* (2013.01); *A61B 1/05* (2013.01); *H04N 23/555* (2023.01)

(58) Field of Classification Search

CPC ......... A61B 1/0011; A61B 1/05; A61B 1/051; G02B 23/2484; H04N 23/54; H04N 23/555

See application file for complete search history.

(56) References Cited

U.S. PATENT DOCUMENTS

| | | | | |
|---|---|---|---|---|
| 9,253,386 B2 * | 2/2016 | Miyazaki | ............... | H04N 23/57 |
| 2006/0264704 A1 * | 11/2006 | Fujimori | ................ | H05K 1/189<br>600/101 |
| 2011/0155317 A1 * | 6/2011 | Shinoda | .............. | B32B 37/1284<br>156/285 |
| 2011/0199473 A1 * | 8/2011 | Kojima | .................. | H04N 7/183<br>257/E23.01 |
| 2013/0128020 A1 * | 5/2013 | Fujimori | ............... | H10F 39/804<br>257/432 |

(Continued)

FOREIGN PATENT DOCUMENTS

WO 2022244133 A1 11/2022

*Primary Examiner* — Peter D Le

(74) *Attorney, Agent, or Firm* — Scully, Scott, Murphy & Presser, P.C.

(57) ABSTRACT

An image pickup module includes: an imager including a light receiving surface; and a back surface opposite to the light receiving surface; a wiring board including a first surface, a bottom surface disposed in a recess surrounded by a plurality of walls, a plurality of electronic components configured to mount on the bottom surface; and a cutout communicating a first space between the back surface and the first surface with a second space inside the recess, the cutout being on a first wall of the plurality of walls; and a resin disposed in the first space, the second space and a third space inside of the cutout, in which the resin is continuous without an interface between the first space, the second space, and the third space.

16 Claims, 8 Drawing Sheets

(56) References Cited

U.S. PATENT DOCUMENTS

| | | | | |
|---|---|---|---|---|
| 2016/0254214 | A1* | 9/2016 | Makino | H01L 23/49541 257/676 |
| 2017/0311786 | A1* | 11/2017 | Maeda | A61B 1/051 |
| 2018/0242826 | A1* | 8/2018 | Shimohata | A61B 1/041 |
| 2020/0337539 | A1* | 10/2020 | Shimohata | H10F 39/804 |
| 2021/0250473 | A1* | 8/2021 | Suyama | A61B 1/0011 |

* cited by examiner

IMAGE PICKUP MODULE, ENDOSCOPE, AND METHOD FOR MANUFACTURING IMAGE PICKUP MODULE

RELATED APPLICATION DATA

This application is based on and claims priority under 35 U.S.C. § 119 to U.S. Provisional Application No. 63/530,538, filed on Aug. 3, 2023, the entire contents of which are incorporated herein by reference.

BACKGROUND

1. Field

The present disclosure relates to an image pickup module in which electronic components are mounted on a wiring board, an endoscope including the image pickup module in which the electronic components are mounted on the wiring board, and a method for manufacturing the image pickup module in which the electronic components are mounted on the wiring board.

2. Description of the Related Art

International Publication No. 2022/244133 discloses an image pickup module including an imager, a three-dimensional wiring board bonded to the imager and including a bank in a frame shape, a plurality of electronic components housed in the bank, and an underfill resin disposed in the bank. In other words, in the three-dimensional wiring board, the bank in a frame shape is included on a side surface and the plurality of electronic components are mounted on a bottom surface of a recess formed by the bank. The bank prevents the underfill resin from spreading to the surrounding area.

The bank is provided with a cutout that is a dent for filling the bank with the underfill resin. Note that the underfill resin is distinguished from a sealing resin disposed in a bonding portion between the imager and the three-dimensional wiring board.

SUMMARY

An image pickup module of an embodiment includes: an imager including a light receiving surface and a back surface opposite to the light receiving surface; a wiring board including a first surface, a bottom surface disposed in a recess surrounded by a plurality of walls, a plurality of electronic components configured to mount on the bottom surface, and a cutout communicating a first space between the back surface and the first surface with a second space inside the recess, the cutout being on a first wall of the plurality of walls; and a resin disposed in the first space, the second space and a third space inside of the cutout, in which the resin is continuous without an interface between the first space, the second space, and the third space.

An endoscope of an embodiment includes an image pickup module disposed in a distal end portion of an insertion portion, in which the image pickup module includes: an imager including a light receiving surface and a back surface opposite to the light receiving surface a wiring board including a first surface a bottom surface disposed in a recess surrounded by a plurality of walls, a plurality of electronic components configured to mount on the bottom surface, and a cutout communicating a first space between the back surface and the first surface with a second space inside the recess, the cutout being on a first wall of the plurality of walls; and a resin disposed in the first space, the second space and a third space inside of the cutout, in which the resin is continuous without an interface between the first space, the second space, and the third space.

A method for manufacturing an image pickup module of an embodiment includes: producing an imager including a light receiving surface and a back surface opposite to the light receiving surface, a plurality of external electrodes disposed on the back surface, and producing a wiring board including a first surface, a plurality of bonding electrodes being disposed on the first principal surface, a bottom surface disposed in a recess surrounded by a plurality of walls, and a cutout communicating a space between the back surface and the first surface with an inside the recess, the cutout being on a first wall of the plurality of walls; mounting a plurality of electronic components on the bottom surface; bonding the plurality of external electrodes and the plurality of bonding electrodes, respectively, using a plurality of bonding agent; and injecting a liquid resin to continuously fill each of the recess, the cutout and the space between the back surface and the first surface; and curing the resin in each of the recess, the cutout and the gap.

DETAILED DESCRIPTION

First Embodiment

Figure 1:
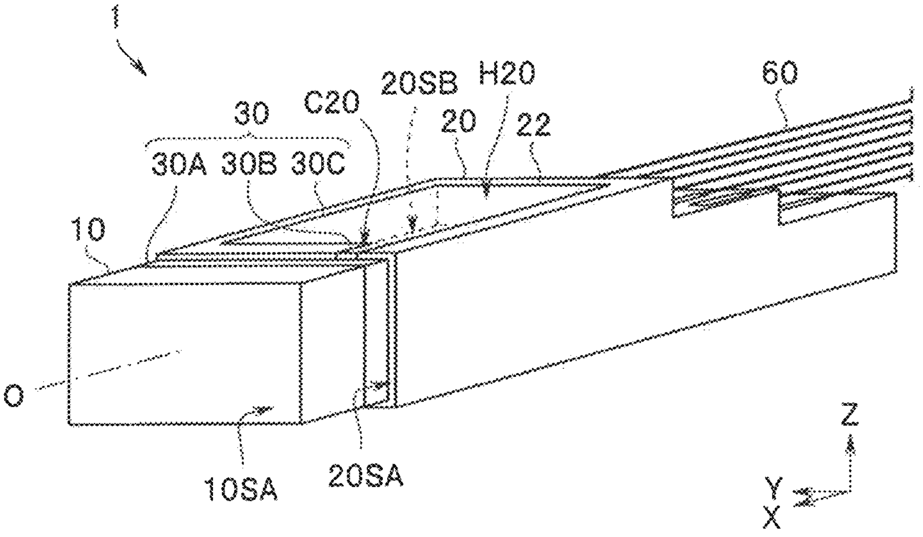
FIG. 1 is a perspective view of an image pickup module of a first embodiment.
Figure 2:
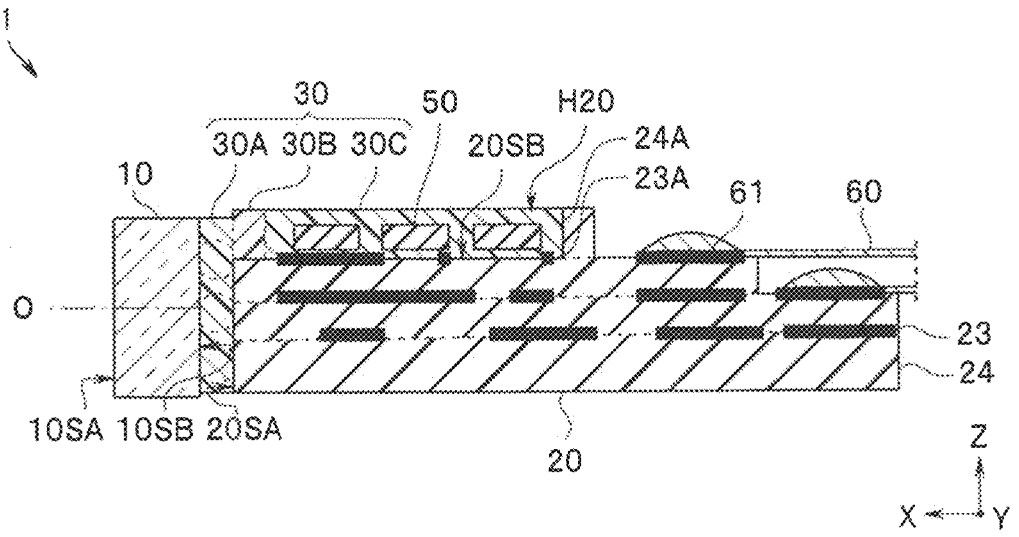
FIG. 2 is a cross-sectional view of the image pickup module of the first embodiment.
Figure 3:
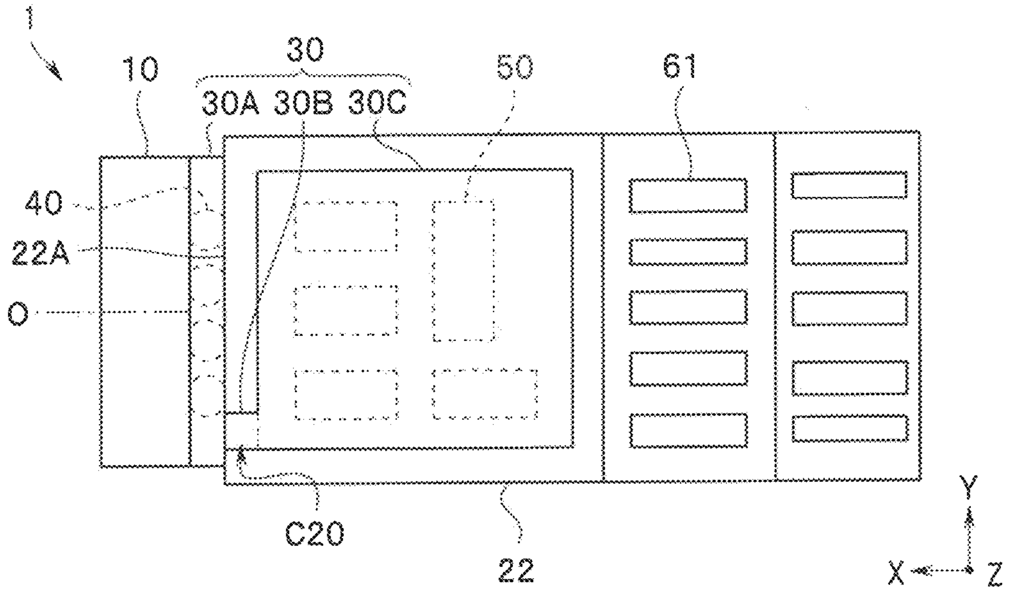
FIG. 3 is a top view of the image pickup module of the first embodiment.

FIG. 1, FIG. 2, and FIG. 3 show an image pickup module 1 of the present embodiment. The image pickup module 1 includes an imager 10 as a semiconductor package, a wiring board 20, a resin 30, solder 40 as a bonding member, electronic components 50, and cables 60.

Note that in the following description, the drawings based on the embodiments are schematic illustrations. The relation between the thickness and the width of each portion, the ratio in thickness of each portion, and the like differ from the actual relation, ratio, and the like. There are also some portions with different dimensional relations and ratios among the drawings. Illustration of and assignment of reference signs to some of the components will be omitted. Note that in the drawings, in a three-axis orthogonal coordinate system, a direction in which an X-axis value increases is referred to as "front" and a direction in which the X-axis value decreases is referred to as "rear." A direction in which a Z-axis value increases is referred to as "up."

The imager 10 includes a light receiving surface 10SA and a back surface 10SB on a side opposite to the light receiving surface 10SA. A plurality of external electrodes 11 are disposed on the back surface 10SB. The imager 10 includes an image sensor, such as a CMOS image sensor or a CCD image sensor, which picks up an image of a subject in a direction of an optical axis O.

In the semiconductor package, a cover glass may be adhesively bonded to the light receiving surface 10SA of the imager 10. In the semiconductor package, one or more semiconductor devices that process image pickup signals are stacked on the back surface of the imager 10 and the external electrodes 11 may be disposed on the back surface 10SB of the semiconductor devices.

The wiring board 20 includes a first principal surface 20SA (first surface) and a second principal surface 20SB (bottom surface) that is a side surface orthogonal to the first principal surface 20SA. A plurality of bonding electrodes 21 are disposed on the first principal surface 20SA. The second principal surface 20SB is a bottom surface of a recess H20 surrounded by a plurality of walls 22 arranged in a frame shape. Of the four walls 22 arranged in the frame shape, a first wall 22A has a cutout C20 communicating with the first principal surface 20SA. In other words, the cutout C20 communicates a first space between the back surface 10SB and the first principal surface 20SA with a second space inside the recess H20. The cutout C20 is provided at an end of the first wall 22A.

The wiring board 20 is a stacked wiring board in which a plurality of wiring layers 23 and a plurality of insulating layers 24 are stacked. For example, the wiring board 20 is manufactured by stacking and firing a green sheet including the wiring layers 23 and the insulating layers 24.

Of the plurality of insulating layers 24, an uppermost first insulating layer 24A constitutes the plurality of walls 22. Therefore, a depth DC20 of the cutout C20 communicating with the first principal surface 20SA is the same as a thickness T24 of the first insulating layer 24A.

A plurality of electronic components 50 are mounted on the second principal surface 20SB. Of the plurality of wiring layers 23, an uppermost first wiring layer 23A constitutes the second principal surface 20SB. In other words, lands (not shown) to which the electronic components 50 are solder-bonded are composed of the first wiring layer 23A. The electronic component 50 is, for example, a capacitor, an inductor, or an IC.

On a side surface where the wiring layers 23 are exposed in the rear of the wiring board 20, lands 61 to which the cables 60 are solder-bonded are disposed. The lands 61 are composed of the wiring layers 23. On the lands, for example, a two-layer plated film consisting of a nickel layer and a gold layer may be disposed.

Figure 4A:
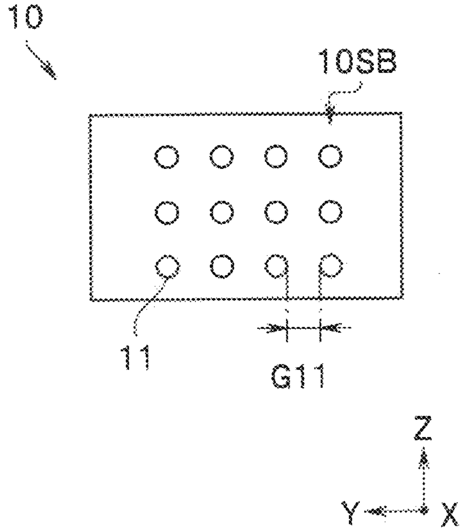
FIG. 4A is a plan view of a back surface of an imager of the image pickup module of the first embodiment.
Figure 4B:
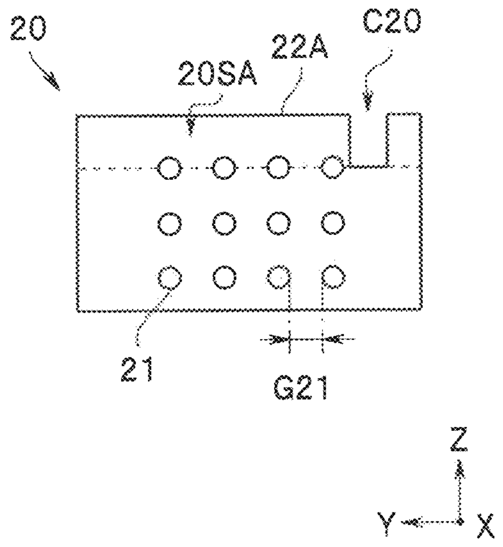
FIG. 4B is a plan view of a first principal surface of a wiring board of the image pickup module of the first embodiment.

The plurality of external electrodes 11 and the plurality of bonding electrodes 21 are respectively bonded by the respective plurality of bonding members. The bonding member (bonding agent) is the solder 40. As shown in FIG. 4A and FIG. 4B, the arrangement of the plurality of external electrodes 11 and a gap G11 correspond to the arrangement of the plurality of bonding electrodes 21 and a gap G21.

The resin 30 includes a first resin 30A, a second resin 30B, and a third resin 30C. The first resin 30A is disposed between the back surface 10SB of the imager 10 and the first principal surface 20SA of the wiring board 20. In other words, the first resin 30A is disposed in the first space. Since the bonding portion formed by the solder 40 is sealed with the first resin 30A, the image pickup module 1 is highly reliable.

The second resin 30B is disposed in the cutout C20 of the wiring board 20. In other words, the second resin 30B is disposed in a third space inside of the cutout C20. The third resin 30C is disposed in the recess H20 of the wiring board 20. In other words, the third resin 30C is disposed in the second space. Since the bonding portions of the electronic components 50 are sealed with the third resin 30C, the image pickup module 1 is highly reliable. Note that the third resin 30C only needs to cover the bonding portions of the electronic components 50 and does not necessarily reach an upper surface of the walls 22.

There is no interface between the first resin 30A and the second resin 30B. There is no interface between the second resin 30B and the third resin 30C. The first resin 30A, the second resin 30B, and the third resin 30C are the integrated same resin 30 (i.e., a continuous resin). In other words, the first resin 30A and the third resin 30C are connected by the second resin 30B.

The resin 30 is, for example, a thermosetting resin, such as an epoxy resin, an acrylic resin, a polyimide resin, a silicone resin, and a polyvinyl resin. The thermosetting resin is liquid before being cured.

As will be described later, since the first resin 30A, the second resin 30B, and the third resin 30C are the same resin simultaneously disposed, air bubbles do not remain between the first resin 30A, the second resin 30B, and the third resin 30C, whereby the bonding portions can be sealed without a gap, and therefore, the image pickup module 1 is highly reliable and can be easily manufactured.

<Method for Manufacturing Image Pickup Module>

Figure 5:
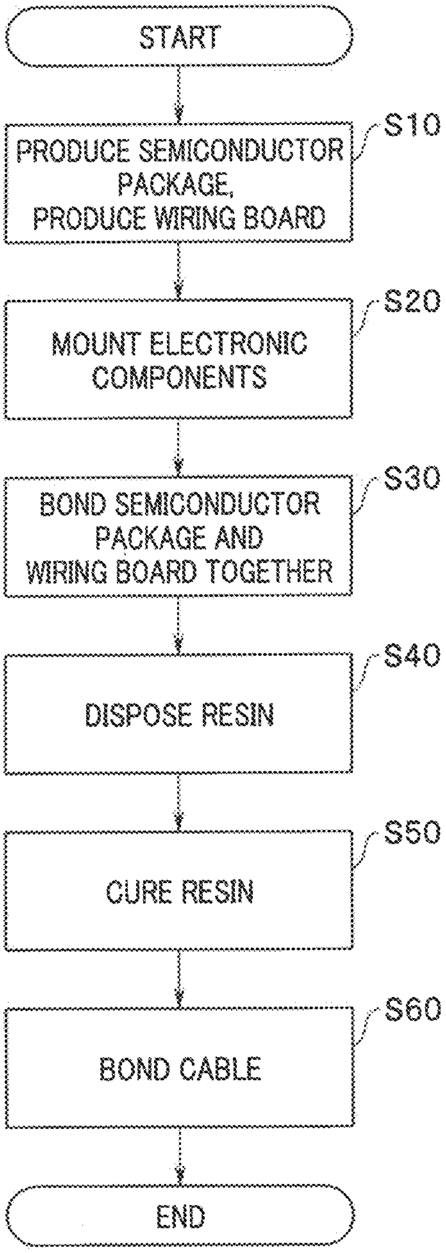
FIG. 5 is a flowchart of a method for manufacturing the image pickup module of the first embodiment.

A method for manufacturing the image pickup module will be described following a flowchart of FIG. 5.

<Step S10> Producing Semiconductor Package, Producing Wiring Board

An image pickup wafer including a plurality of image pickup circuits each including a CMOS light receiving element or the like is produced using a publicly-known method for manufacturing a semiconductor. A glass wafer is adhesively bonded to the image pickup wafer. The image pickup wafer to which the glass wafer is adhesively bonded is cut, so that the imager 10 as a semiconductor package, which includes the light receiving surface 10SA and the back surface 10SB and includes the plurality of external electrodes 11 on the back surface 10SB, is produced. The solder 40 that constitutes solder bumps is disposed on each of the plurality of external electrodes 11.

A plurality of wiring sheets are stacked and fired, so that the wiring board 20 is produced. The wiring sheet is an unfired member generally referred to as a green sheet and includes predetermined surface wiring and through wiring. The wiring board 20 may be a multi-layer wiring board in which a plurality of resin layers and a plurality of wiring layers are stacked. The wiring board 20 may be a MID (molded interconnect device).

<Step S20> Mounting Electronic Component

The plurality of electronic components 50 are mounted on the bottom surface, which is the second principal surface 20SB of the wiring board 20, of the recess H20 surrounded by the walls 22. In other words, the electronic components 50 are solder-bonded to the lands (not shown) of the first wiring layer 23A.

<Step S30> Bonding Semiconductor Package and Wiring Board Together

The external electrodes 11 on the back surface 10SB of the imager 10 as a semiconductor package and the bonding electrodes 21 on the first principal surface 20SA of the wiring board 20 are bonded together using the solder 40.

<Step S40> Disposing Resin

Figure 6:
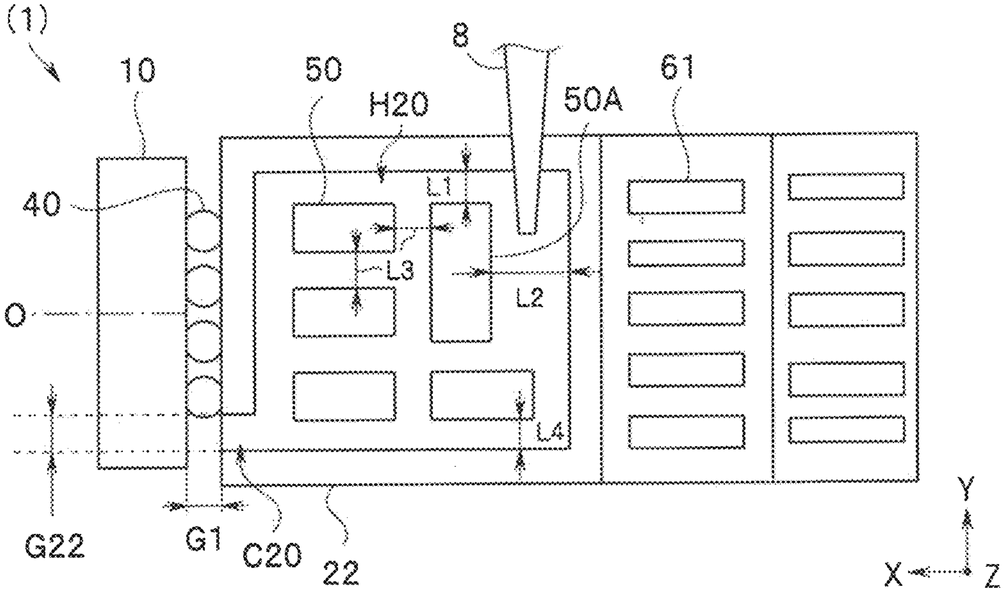
FIG. 6 is a top view for explaining the method for manufacturing the image pickup module of the first embodiment.

As shown in FIG. 6, an uncured liquid resin is injected into the recess H20 through a nozzle 8 of a dispenser. The viscosity (25° C.) of the liquid resin 30 is, for example, 40 pa·s. The liquid resin 30 injected into the recess H20 spreads, via the cutout C20, between the back surface 10SB of the imager 10 and the first principal surface 20SA of the wiring board 20, that is, to the bonding portion formed by the solder 40.

Since the resin 30 injected from one portion spreads, the first resin 30A between the back surface 10SB of the imager 10 and the first principal surface 20SA of the wiring board 20, the second resin 30B of the cutout C20, and the third resin 30C of the recess H20 consist of the integrated same resin 30. Therefore, there is no interface between the first resin 30A, the second resin 30B, and the third resin 30C, whereby air bubbles do not remain.

In order to cause the liquid resin injected into the recess H20 to efficiently flow and spread to the bonding portion formed by the solder 40, the interfacial tension is used. Therefore, as shown in FIG. 6, a first gap G1 that is a distance between the back surface 10SB of the imager 10 and the first principal surface 20SA of the wiring board 20 and a width G22 of the cutout C20 can be less than 0.5 mm.

Figure 7:
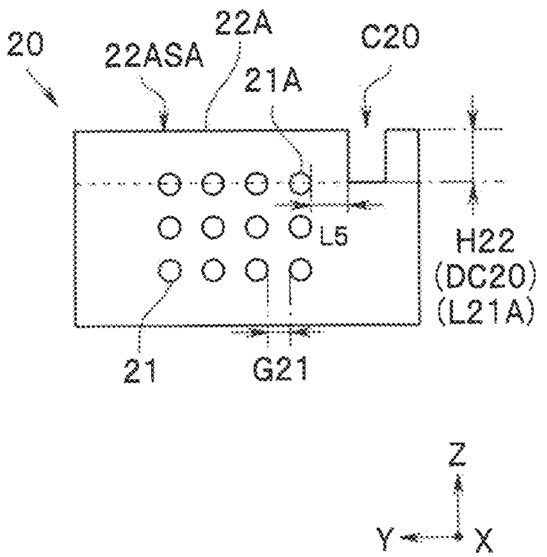
FIG. 7 is a plan view of the back surface of the imager of the image pickup module of the first embodiment.
Figure 8:
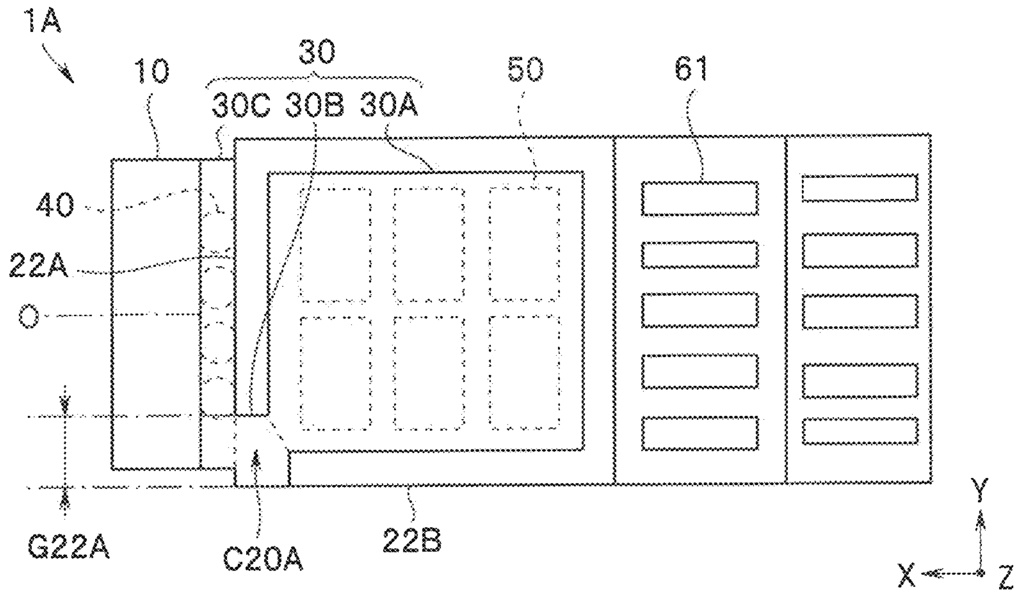
FIG. 8 is a top view of an image pickup module of a modification of the first embodiment.
Figure 9:
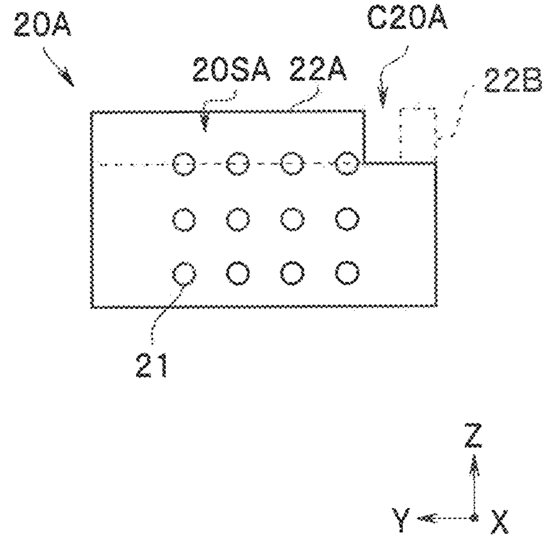
FIG. 9 is a plan view of the first principal surface of a wiring board of the image pickup module of the modification of the first embodiment.

In order to more surely flow and spread the resin 30 to the bonding portion formed by the solder 40, as shown in FIG. 7, the depth DC20 (height H22 of the walls 22) of the cutout C20 can be substantially the same as a distance L21A from a center of a bonding electrode 21A most adjacent to the cutout C20 to an upper surface 22ASA of the first wall 22A. For example, the depth DC20 is more than 90% and less than 110% of the distance L21A.

Further, distances L1, L2 between an electronic component 50A closest to a position where a distal end of the nozzle 8 is arranged and the wall 22, a gap L3 between the electronic components 50, a distance LA between the electronic components 50 other than the electronic component 50A and the wall 22, the width G22 of the cutout C20, a distance L5 between the cutout C20 and the bonding electrode 21A closest to the cutout C20, and the gap G21 between the bonding electrodes 21 can satisfy Formula 1 below.

$$L1, L2 \geq L3 \geq LA \geq G22 \geq L5 \geq G21 \quad \text{<Formula 1>}$$

<Step S50> Curing Resin

The liquid resin 30 is heat-treated to become the resin 30 in a solid form. When the temperature rises at an initial stage of the heat treatment, the viscosity of the liquid resin 30 decreases as compared to the viscosity at room temperature, and thus, the resin 30 further spreads due to the interfacial tension.

<Step S60> Bonding Cable

The cables 60 are bonded to the lands 61 of the wiring board 20.

As described above, in the method for manufacturing the image pickup module of the present embodiment, the imager 10 as a semiconductor package and the wiring board 20 are bonded together using the solder 40 as a bonding member. Further, the resin 30 is disposed between the back surface 10SB and the first principal surface 20SA, the cutout C20, and the recess H20. In disposing the resin 30, the resin 30 in a liquid form is injected through the recess H20. The resin 30 spread between the back surface 10SB and the first principal surface 20SA, the cutout C20, and the recess H20 is treated by curing.

According to the method for manufacturing the image pickup module of the present embodiment, the plurality of bonding portions can be surely and easily sealed with resin. In other words, according to the method for manufacturing the image pickup module of the present embodiment, the highly reliable image pickup module can be easily manufactured.

Modification of First Embodiment

An image pickup module 1A of a modification of the first embodiment is similar to and has the same effects as the effects of the image pickup module 1 of the embodiment. Therefore, in the following description, the same components as the components of the image pickup module 1 will be assigned the same reference signs and the descriptions will be omitted.

As shown in FIG. 8 to FIG. 11, in the image pickup module 1A, a width G22A of a cutout C20A of the wall 22 of a wiring board 20A is larger than the width G22 of the cutout C20 of the image pickup module 1.

The cutout C20A cuts out not only the first wall 22A, but also a second wall 22B orthogonal to the first wall 22A.

Figure 10:
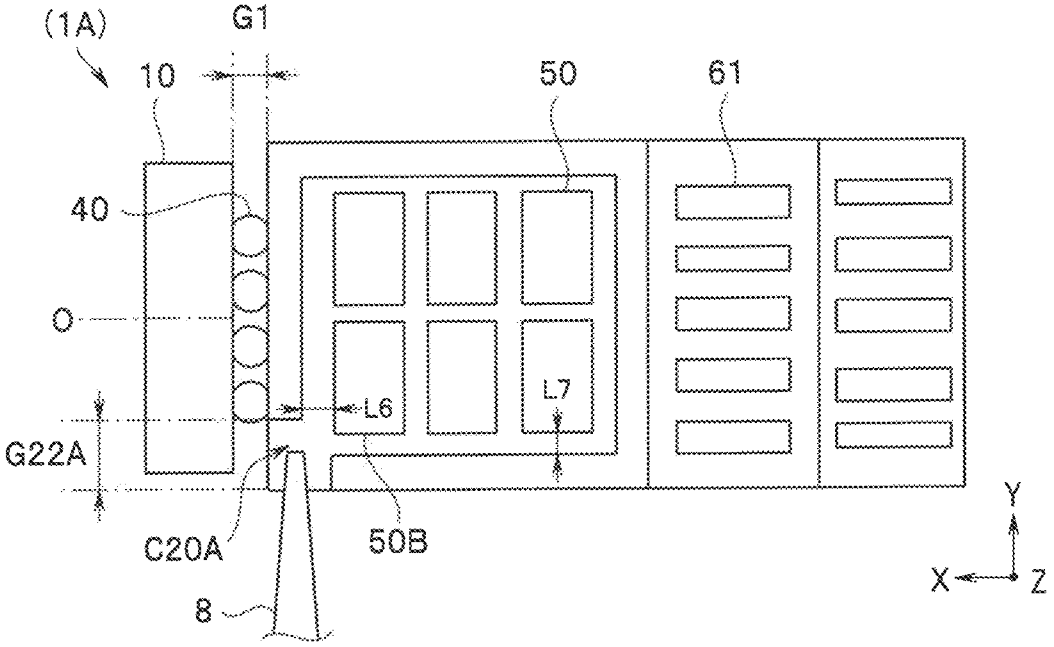
FIG. 10 is a top view for explaining a method for manufacturing the image pickup module of the modification of the first embodiment.
Figure 11:
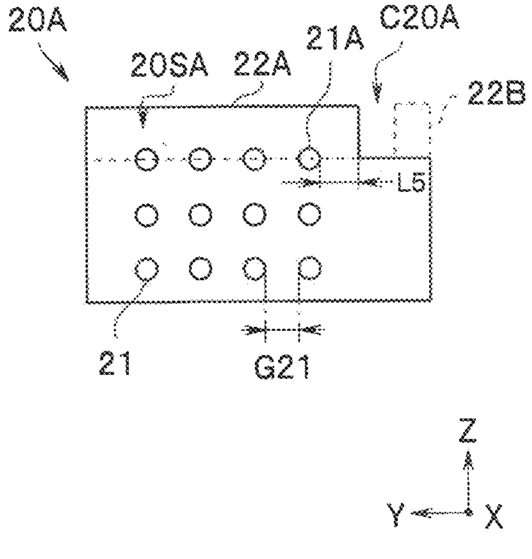
FIG. 11 is a plan view of the back surface of the imager of the image pickup module of the modification of the first embodiment.

As shown in FIG. 10, at the time of manufacturing the image pickup module 1A, the resin 30 is injected through the cutout C20A. In other words, the distal end of the nozzle 8 is arranged in the cutout C20A so that the resin 30 is injected.

In the image pickup module 1A, the distance L5 between the cutout C20A and the bonding electrode 21A closest to the cutout C20A, the gap G21 between the bonding electrodes 21, a distance L6 between an electronic component 50B closest to the cutout C20A and the wall 22, and a distance L7 between the electronic components 50 other than the electronic component 50B and the wall 22 can satisfy Formula 2 below.

$$L5 \geq G21, L6 \geq L7 \quad \text{<Formula 2>}$$

Second Embodiment

An image pickup module 1B of a second embodiment and an image pickup module 1C of a modification of the second embodiment are similar to and have the same effects as the effects of the image pickup modules 1, 1A. Therefore, in the following description, the same components as the components of the image pickup modules 1, 1A will be assigned the same reference signs and the descriptions will be omitted.

Figure 12:
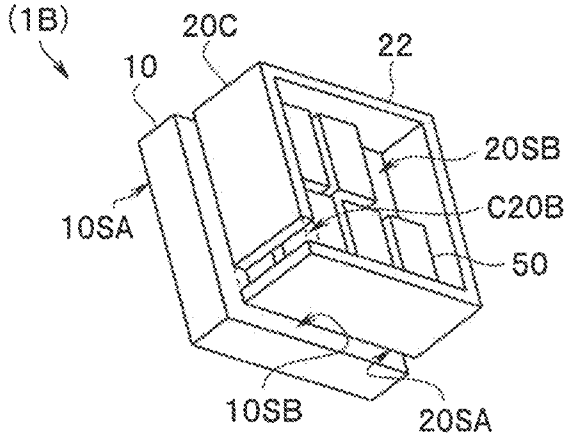
FIG. 12 is a perspective view of an image pickup module of a second embodiment.

In the image pickup module 1B shown in FIG. 12, the second principal surface 20SB, on which the electronic components 50 are mounted, of a wiring board 20B is a rear surface on a side opposite to the first principal surface 20SA. A cutout C20B communicates with the first principal surface 20SA.

Though not shown, the cables 60 are bonded to lands on an outer surface of the wall 22.

The image pickup module 1B has a shorter length in an optical axis direction and is smaller than the image pickup module 1.

Modification of Second Embodiment

Figure 13:
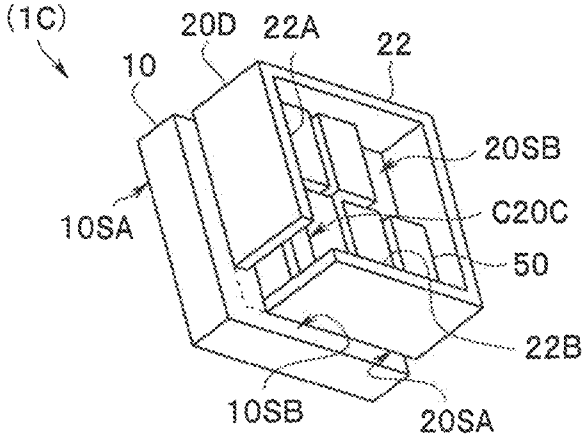
FIG. 13 is a perspective view of an image pickup module of a modification of the second embodiment.

In the image pickup module 1C shown in FIG. 13, as with the image pickup module 1A, a cutout C20C cuts out not only the first wall 22A, but also the second wall 22B.

Third Embodiment

Figure 14:
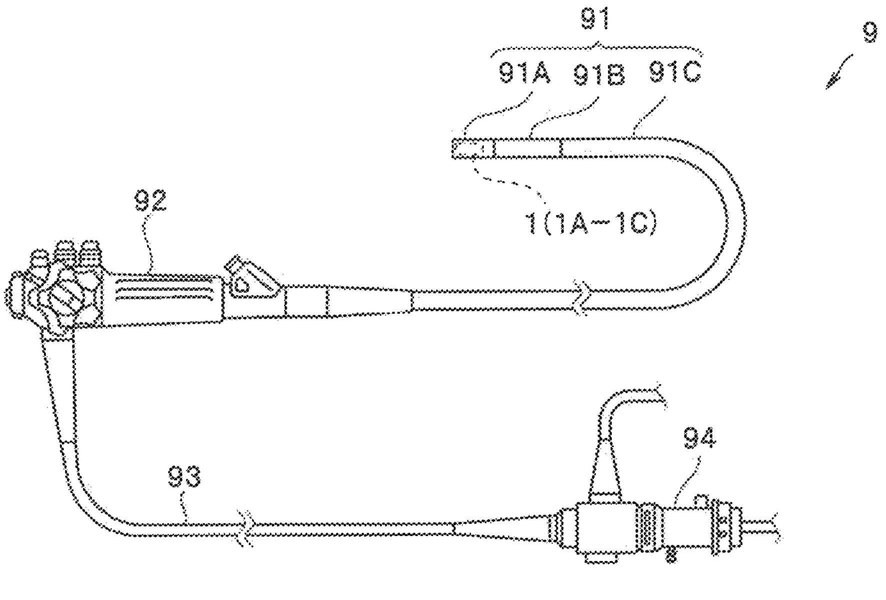
FIG. 14 is a perspective view of an endoscope of a third embodiment.

An endoscope 9 of the present embodiment shown in FIG. 14 includes an insertion portion 91, an operation portion 92, a universal cord 93, and a connector 94.

The insertion portion 91 in an elongated tubular shape is inserted into a body cavity of a living body. The insertion portion 91 is continuously provided with a distal end portion 91A, a bending portion 91B, and a flexible tube 91C in order from the distal end side and is generally flexible. The image pickup module 1 (1A to 1C) is arranged inside the distal end portion 91A. The bending portion 91B bends in up, down, left, and right directions in accordance with the rotating operation of a bending knob of the operation portion 92 for performing bending operation.

The flexible tube 91C is a flexible tubular member that is passively flexible. A treatment instrument channel, a signal wire, a fiber bundle, and the like are inserted through the inside of the flexible tube 91C. The signal wire extends from the image pickup module 1 (1A to 1C) in the distal end portion 91A through the operation portion 92 to the universal cord 93. The fiber bundle guides the light from a light source device that is external equipment to a distal end surface of the distal end portion 91A.

The operation portion 92 is provided continuously with a proximal end portion of the insertion portion 91 and includes a plurality of operation members and the like. The universal cord 93 extends from the operation portion 92. The connector 94 is a connecting member for connecting the universal cord 93 and the external equipment.

As already described, since the image pickup module 1 is highly reliable, the endoscope 9 is highly reliable. It goes without saying that the endoscope 9 including the image pickup modules 1A to 1C has the effects of the image pickup modules 1A to 1C.

The endoscope 9 of the embodiment may be a flexible endoscope with the insertion portion 91 that is flexible or a rigid endoscope with the insertion portion 91 that is rigid. The endoscope 9 may be for either medical use or industrial use.

The present invention is not limited to the aforementioned embodiments and the like, and various changes, combinations, and applications are available within the scope without departing from the gist of the invention.

What is claimed is:

1. An image pickup module comprising:
an imager including:
a light receiving surface; and
a back surface opposite to the light receiving surface;
a wiring board including:
a first surface;
a bottom surface disposed in a recess surrounded by a plurality of walls, a plurality of electronic components configured to mount on the bottom surface, and
a cutout communicating a first space between the back surface and the first surface with a second space inside the recess, the cutout being on a first wall of the plurality of walls; and
a resin disposed in the first space, the second space and a third space inside of the cutout,
wherein the resin is continuous without an interface between the first space, the second space, and the third space.

2. The image pickup module according to claim 1, wherein the resin includes:
a first resin disposed in the first space,
a second resin disposed in the second space, and
a third resin disposed in the third space,
wherein the first resin, the second resin and the third resin are without the interface between each other.

3. The image pickup module according to claim 1, further comprising:
a plurality of external electrodes disposed on the back surface,
a plurality of bonding electrodes disposed on the first surface, and
a plurality of bonding agent each bonding the plurality of external electrodes and the plurality of bonding electrodes, respectively.

4. The image pickup module according to claim 3, wherein a depth of the cutout is equal to a distance from a center of a bonding electrode of the plurality of bonding electrodes that is most adjacent to the cutout to an upper surface of the first wall.

5. The image pickup module according to claim 3, wherein a width of the cutout is equal to or larger than a gap between adjacent bonding electrodes of the plurality of bonding electrodes.

6. The image pickup module according to claim 1, wherein
the wiring board is a stacked wiring board in which a plurality of wiring layers and a plurality of insulating layers are stacked,
the plurality of walls comprise a first insulating layer of the plurality of insulating layers, and
the bottom surface comprises a first wiring layer of the plurality of wiring layers.

7. The image pickup module according to claim 6, wherein a depth of the cutout is a same as a thickness of the first insulating layer.

8. The image pickup module according to claim 1, wherein the cutout is provided at an end of the first wall.

9. The image pickup module according to claim 1, wherein a gap between the back surface and the first surface and a width of the cutout are each less than 0.5 mm.

10. The image pickup module according to claim 1, wherein the bottom surface is proximal to the first surface.

11. The image pickup module according to claim 10, wherein the bottom surface is orthogonal to the first surface.

12. The image pickup module according to claim 10, wherein the bottom surface is along the first surface.

13. The image pickup module according to claim 1, wherein the cutout further being on a second wall of the plurality of walls, the second wall is intersecting with the first wall.

14. An endoscope comprising:
the image pickup module according to claim 1 disposed in a distal end portion of an insertion portion.

15. A method for manufacturing an image pickup module, the method comprising:

producing an imager including:

a light receiving surface;

a back surface opposite to the light receiving surface, a plurality of external electrodes disposed on the back surface, and producing a wiring board including:

a first surface, a plurality of bonding electrodes being disposed on the first principal surface;

a bottom surface disposed in a recess surrounded by a plurality of walls, and a cutout communicating a space between the back surface and the first surface with an inside the recess, the cutout being on a first wall of the plurality of walls;

mounting a plurality of electronic components on the bottom surface;

bonding the plurality of external electrodes and the plurality of bonding electrodes, respectively, using a plurality of bonding agent; and injecting a liquid resin to continuously fill each of the recess, the cutout and the space between the back surface and the first surface; and curing the resin in each of the recess, the cutout and the gap.

16. The method for manufacturing the image pickup module according to claim 15, wherein the liquid resin is injected from the cutout.

* * * * *